United States Patent [19]

Robins et al.

[11] Patent Number: 4,992,426

[45] Date of Patent: Feb. 12, 1991

[54] ANTIPARASITIC 5'-SULFAMOYL NUCLEOSIDES

[75] Inventors: Roland K. Robins, Irvine; Ganesh D. Kini, Costa Mesa, both of Calif.

[73] Assignee: Nucleic Acid Research Institute, Costa Mesa, Calif.

[21] Appl. No.: 316,421

[22] Filed: Feb. 27, 1989

[51] Int. Cl.$^5$ .............................................. A61K 31/70
[52] U.S. Cl. .......................................... 514/43; 536/23
[58] Field of Search ...................... 536/23, 24; 514/42, 514/43

[56] References Cited

U.S. PATENT DOCUMENTS

Re. 29,835 11/1978 Witkowski et al. .................. 536/23

OTHER PUBLICATIONS

Smee et al., Antiviral Research, vol. 10, pp. 253–262 (1988) (Dec.).

Primary Examiner—John W. Rollins
Assistant Examiner—James O. Wilson

[57] ABSTRACT

The triazole nucleosides 1-(5'-O-sulfamoyl-β-D-ribofuranosyl)[1,2,4]triazole-3-carboxamide, 1-(5'-O-sulfamoyl-β-D-ribofuranosyl)[1,2,4]triazole-3-thiocarboxamide and 1-(5'-O-sulfamoyl-β-D-ribofuranosyl)[1,2,4]triazole-3-carbonitrile are prepared and used as antiparasitic agents.

7 Claims, No Drawings

ANTIPARASITIC 5'-SULFAMOYL NUCLEOSIDES

BACKGROUND OF THE INVENTION

This invention is directed to triazole nucleosides and to their use as antiparasitic agent particularly the triazole nucleosides 1-(5'-0-sulfamoyl-β-D-ribofuranosyl)[1,2,4]triazole-3-carboxamide, 1-(5'-0-sulfamoyl-β-D-ribofuranosyl)[1,2,4]triazole-3-thiocarboxamide and 1-(5'-O-sulfamoyl-β-D-ribofuranosyl)[1,2,4]triazole-3-carbonitrile.

Parasitic diseases are a scourge of essentially all higher organisms. The protozoa and other pathogens which cause these diseases are wide spread and cause much pain, suffering and economic loss world wide. Control of certain of these pathogens is difficult because of the life cycle of the parasite is divided between a vector and a further host or hosts. Invertebrates can often serve as the vector as, for instance, in the various forms of trypanosomiasis and leishmaniasis. In other of there parasitic disease, e.g. trichomoniasis, the parasite can be spread directly within a species often times between the sexes of that species and in further parasitic diseases such as giardiasis spread is from one species to a different species.

Certain nucleosides have been shown to exhibit antiparasitic properties. The first chemical synthesis of a sulfamoyl nucleoside, 5'-O-sulfamoyl adenosine, was reported by D. A. Shuman, M. J. Robins and R. K. Robins, J. Am. Chem. Soc., 1969, 91, 3434 (1969). Unfortunately while 5'-sulfamoyl adenosine was active in-vitro against certain parasites, it was also found to be extremely toxic.

1-(β-D-Ribofuranosyl)[1,2,4]triazole-3-carboxamide (Ribavirin), is a relatively non-toxic broad spectrum antiviral agent. It has also been shown to be a substrate for adenosine kinase in certain human cell lines in-vitro. It however does not have antiparasitic activity.

BRIEF DESCRIPTION OF THE INVENTION

The present invention relates to a novel class of 5'-sulfamoyl nucleoside and their use as antiparasitic agents.

In accordance with this invention the compounds 1-(5'-O-sulfamoyl-β-D-ribofuranosyl)[1,2,4]triazole-3-carboxamide, 1(5'-Q-sulfamoyl-β-O-ribofuranosyl)[1,2,4]triazole-3-thiocarboxamide and 1-(5'-Q-sulfamoyl-β-D-ribofuranosyl)[1,2,4]triazole-3-carbonitrile are prepared and use as antiparasitic agents.

The compounds of the invention are effective as antiparasitic agents particular against protozoal infections including trypanosomiasis, leishmaniasis, trichomoniasis and giardiasis A salient feature of the invention is a method of treating parasitic disease wherein a host afflicted with such a parasitic disease is administered a composition containing as its active ingredient an antiparasitic effective amount of a compound selected from 1-(5'-O-sulfamoyl-β-D-ribofuranosyl)[1,2,4]triazole-3-carboxamide, 1-(5'-O-sulfamoyl-β-D-ribofuranosyl)[1,2,4]triazole-3-thiocarboxamide and 1-(5'-O-sulfamoyl-β-D-ribofuranosyl)n[1,2,4]triazole-3-carbonitrile.

A particular advantage of this method is the treatment of the protozoal infections trypanosomiasis, leishmaniasis, trichomoniasis and giardiasis.

Particularly useful in the treatment of parasitic diseases are pharmaceutical compositions including an antiparasitic effective amount of a compound selected from 1-(5'-O-sulfamoyl-β-D-ribofuranosyl)[1,2,4]triazole-3-carboxamide, 1-(5'-O-sulfamoyl-β-D-ribofuranosyl)[1,2,4]triazole-3-thiocarboxamide and 1-(5'-O-sulfamoyl-β-D-ribofuranosyl)[1,2,4]triazole-3-carbonitrile.

Still further benefits and advantages of the present invention will be apparent to those skilled in the art from the following examples, descriptions, tables and claims as are set forth in the remainder of this specification.

DETAILED DESCRIPTION OF THE INVENTION

For the preparation of 5'-sulfamoyl derivatives of 1-(β-D-ribofuranosyl)[1,2,4]triazole-3-carboxamide, 1-(β-D-ribofuranosyl)[1,2,4]triazole-3-thiocarboxamide and 1-(β-D-ribofuranosyl)[1,2,4]triazole-3-carbonitrile, suitably triazole nucleosides are first protected and converted to their corresponding 5'-sulfamoyl derivatives, which on subsequent deprotection gave the desired compounds in good yields. The structures of the compounds of the invention were confirmed by X-ray crystallographic analysis. The compounds of the invention were further tested and shown to have significant antiparasitic activity in both in-vitro and in-vivo.

Chemistry:

The synthesis of 1-(5'-O-sulfamoyl-β-D-ribofuranosyl)[1,2,4]triazole-3-carboxamide (2) was accomplished as shown in Scheme I. 1-(β-D-Ribofuranosyl)[1,2,4]triazole-3-carboxamide was converted to its 2',3'-di-O-isopropylidene derivative, 5, by treatment with dimethoxypropane and acetone under acid catalyzed conditions in 58% yield. Treatment of 5 with sulfamoyl chloride and sodium hydride in dry THF yielded the 5'-O-sulfamoyl derivative, 1-(5'-O-sulfamoyl-2',3'-di-O-isopropylidene-β-D-ribofuranosyl)[1,2,4]triazole-3-carboxamide, 6, in 80% yield. The protected nucleoside 6 was subsequently deblocked by treatment with 80% acetic acid to give compound 2 in 79 % yield.

SCHEME I

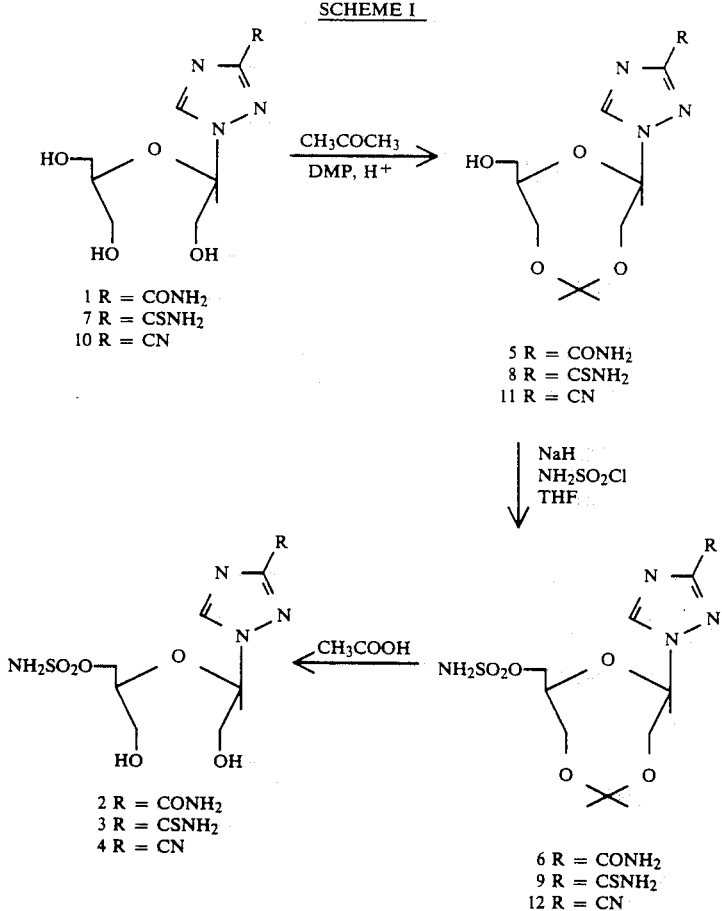

1 R = CONH₂
7 R = CSNH₂
10 R = CN

5 R = CONH₂
8 R = CSNH₂
11 R = CN

2 R = CONH₂
3 R = CSNH₂
4 R = CN

6 R = CONH₂
9 R = CSNH₂
12 R = CN

Scheme I also outlines the synthesis of the thioamide sulfamate, 1-(5'-O-sulfamoyl-β-D-ribofuranosyl)[1,2,4]-triazole-3-thiocarboxamide (3). In a manner similar to the synthesis of 2, 1-(β-D-ribofuranosyl)[1,2,4]triazole-3-thiocarboxamide, 7, prepared as per the procedure of J. T. Witkowski, R. K. Robins, G. P. Khare, R. W. Sidwell, *J. Med. Chem.*, 16, 935 (1973) was converted to the corresponding isopropylidene derivative, 1-(2',3'-di-O-isopropylidene-β-D-ribofuranosyl)[1,2,4]triazole-3-thiocarboxamide, 8. Subsequent treatment with sulfamoyl chloride resulted in the protected sulfamate, 1-(5'-O-sulfamoyl-2',3'-di-O-isopropylidene-β-D-ribofuranosyl)[1,2,4]triazole-3-thiocarboxamide, 9, which was then deblocked by treatment with aqueous acetic acid to give the thioamide sulfamate 3.

1-(5'-O-Sulfamoyl-β-D-ribofuranosyl)[1,2,4]triazole-3carbonitrile (4), was further synthesized according to Scheme I. 2',3',5'-Tri-O-acetyl-1-(β-D-ribofuranosyl)[1,2,4]triazole-3-carbonitrile prepared by the procedure of G. D. Kini, R. K. Robins and T. L. Avery, *J. Med. Chem.*, 1988 (submitted for publication) was deblocked under acidic conditions to yield 1-(β-D-ribofuranosyl)[1,2,4]triazole-3-carbonitrile, 10. Subsequent treatment with acetone and dimethoxypropane in the presence of perchloric acid resulted in the isopropylidene, 1(2',3'-di-O-isopropylidene-β-D-ribofuranosyl)[1,2,4]triazole3-carbonitrile, 11, which was then converted to the sulfamate, 1-(5'-O-sulfamoyl-2',3'-di-O-iso-propylidene-β-D-ribofuranosyl)[1,2,4]-triazole-3-carbonitrile, 12, by treatment with sulfamoyl chloride. Deblocking with aqueous acetic acid gave the cyano triazole sulfamate, 4, in nearly quantitative yield.

The compounds of the invention were found to crystallize readily from appropriate solvents, yielding crystals suitable for X-ray crystallography. Compound 2 crystallized as thick, colorless, transparent plates from a slowly cooled hot ethanol/water solution. Compound 3 crystallized from a slowly cooled hot methanol solution as transparent yellowish square pyramids. Slow cooling of a warm methanol/ether solution of 4 produced colorless, transparent pentagonally-cross-sectioned needles.

The sugar conformations are $C_2$, exo for 2, $C_2$, endo for 3 and $C_3$, exo for 4 with pseudorotation angles of 340°, 162° and 198°, respectively. The C4'–C5' conformations are qg for 2 and 3 and qt for 4. The glycosidic torsion angle, $O4' \approx C1' \approx N1$-N2, in each structure is 175.0(1)° for 2, 50.6(2)° for 3, and 64.2(2)° for 4.

Despite these differences in the three structures, the sulfamoyl moiety is similarly situated with respect to the ribose ring with the $NH_2$ group over the ring. Every NH and OH in each structure is involved in hydrogen bonding. The amino group of the sulfamoyl moiety in 3 is intramolecularly hydrogen bonded to N2 of the triazole ring.

Proton NMR data were obtained at 300 MHz on an IBM NR-300 spectrometer in $(CD_3)_2SO$ or $CDCl_3$ solvents using the residual proton as internal reference. Melting points were obtained in open capillaries using a Haake-Buchler apparatus and are uncorrected. Combustion analyses were performed by Robertson Laboratories, Florham Park, N.J.

EXAMPLE 1

1-(2′,3′-Di-O-isopropylidene-β-D-ribofuranosyl)[1,2,4]-triazole-3-carboxamide (5)

A suspension of 1-(β-D-ribofuranosyl)[1,2,4]triazole-3-carboxamide (1) (5.0 g, 20.5 mmol) in mixture of acetone (100 mL) and dimethoxypropane (50 mL) was cooled to 0° in an ice bath. Perchloric acid (0.34 mL, 70%) was added dropwise with stirring. The resulting clear solution was stirred at 0° for 1.5h and neutralized to pH 7 by dropwise addition of 1N aqueous sodium hydroxide in cold. The mixture was concentrated in vacuo and the residue chromatographed over silica gel (flash chromatography) with 10% acetone in chloroform as eluent to yield 5 (3.38 g, 58%) as an analytically pure oil which crystallized from methanol; m.p. 163°–165°; $^1$H NMR (300 MHz, DMSOd$_6$)δ1.31, 1.49 (2s, 2H, isopropylidene methyls); 3.40 (m, 2H, C$_5$H); 4.23 (t, 1H, C$_4$H); 4.96 (t,1H, —OH); 4.90, 5.18 (2d, 2H, C$_2$H and C$_3$H); 6.20 (s, 1H, C$_1$H); 7.67, 7.87 (2s, 2H, —CONH$_2$); 8.81 (s, 1H, triazole ring proton). Anal. (C$_{11}$H$_{16}$N$_4$O$_5$) Calcd.: C, 46.48; H, 5.67; N, 19.71. Found: C, 46.19; H, 5.49; N, 19.51.

EXAMPLE 2

1-(5′-O-Sulfamoyl-2′,3′-di-O-isopropylidene-β-D-ribofuranosyl) [1,2,4]triazole-3-carboxamide (6)

A solution of 1-(2′,3′-di-O-isopropylidene-β-D-ribofuranosyl) [1,2,4]triazole-3-carboxamide (5) (10.0 g, 34.9 mmol) in dry tetrahydrofuran (200mL) was cooled to 0° in an ice bath. Sodium hydride (4.2 g, 60% suspension in oil) was added and the mixture stirred for 15 min. A solution of sulfamoyl chloride (9.3 g, 80.5 mmol) in dry tetrahydrofuran (50 mL) was added dropwise and the resulting mixture stirred at 0° for 2h and at room temperature for 4 h. The mixture was cooled after which ethanol (20 mL) and saturated aqueous ammonium chloride (20 mL) were added in succession. The mixture was concentrated in vacuo and chromatographed over silica gel (flash chromatography) with 20% acetone in chloroform to yield 6 (7.8 g, 61.5%) as a colorless oil; $^1$H NMR (DMSO-d$_6$)δ1.33, 1.51 (2s, 6H, isopropylidene methyls); 4.11 (m, 2H, C$_5$H); 4.44 (m, 1H, C$_4$H); 5.02, 5.17 (m, 1H, d, 11H, C$_2$H and C$_3$H); 6.36 (s, 1H, C$_1$H); 7.59 (s, 2H, —SO$_2$NH$_2$); 7.72, 7.88 (2s, 2H, —CONH$_2$); 8.82 (s, 1H, triazole ring proton). Anal. (C$_{11}$H$_{17}$N$_5$O$_7$S) Calcd.: C, 36.36; H, 4.72; N, 19.28; S,8.82. Found: C, 36.37; H, 4.75; N, 19.23; S,8 88.

EXAMPLE 3

1-(2′,3′-Di-O-isopropylidene-β-D-ribofuranosyl)[1,2,4]-triazole-3-thiocarboxamide (8)

A suspension of 1-(-β-D-ribofuranosyl)[1,2,4]triazole-3-thiocarboxamide (7) (5.8 g, 22.3 mmol) in mixture of acetone (100 mL) and dimethoxypropane (50 mL) was treated in a manner identical to the synthesis of compound 5 to yield 8 (5.9 g, 88%) as an analytically pure oil; $^1$H NMR (DMSO-d$_6$) 1.32, 1.50 (2s, 6H, isopropylidene methyls); 3.40 (m, 2H, C$_5$H); 4.98 (t, 1H, —OH); 4.90, 5.17 (2d, 2H, C$_2$H and C$_3$H); 6.18 (s, 1H, C$_1$H); 8.80 (s, 1H, triazole ring proton); 9.55, 10.01 (2s, 2H, CSNH$_2$) Anal. (C$_{11}$H$_{16}$N$_4$O$_4$S) Calcd.: C, 43.99; H, 5.37; N, 18.66; S, 10.67. Found: C, 43.71; H, 5.50; N, 18.44; S, 10.66.

EXAMPLE 4

1-(5′-O-Sulfamoyl-2′,3′-di-O-isopropylidene-β-D-ribofuranosyl) [1,2,4]triazole-3-thiocarboxamide (9)

A solution of 1-(2′,3′-di-O-isopropylidene-β-D-ribofuranosyl)[1,2,4]triazole-3-thiocarboxamide (8) (2.0 g, 6.7 mmol) in dry tetrahydrofuran (50 mL) was cooled to 0° in an ice bath. Sodium hydride (0.80 g, 60% suspension in oil) was added and the mixture stirred for 15 min. A solution of sulfamoyl chloride (1.55 g, 13.4 mmol) in dry tetrahydrofuran (10 mL) was added dropwise and the resulting mixture stirred at 0° for 2 h and at room temperature for 1 h. The mixture was cooled; ethanol (5 mL) and saturated aqueous ammonium chloride (5 mL) were added in succession. The mixture was concentrated in vacuo and chromatographed over silica gel (flash chromatography) with 20% acetone in chloroform to yield 9 (1.8 g, 70%) as a yellow oil; $^1$H NMR (DMSO-d$_6$)δ1.33, 1.52 (2s, 2H, isopropylidene methyls); 4.11 (m, 2H, C$_5$H); 4.44 (m, 1H, C$_4$H); 5.02, 5.16 (d,m, 2H, C$_2$ and C$_3$ Hs); 6.35 (s, 1H, C$_1$H); 7.58 (s, 2H, —SO$_2$NH$_2$); 8.81 (s, 1H, triazole ring proton); 9.55, 10.05 (2s, 2H, —CSNH$_2$). Anal. (C$_{11}$H$_{17}$N$_5$O$_6$S$_2$) Calcd.: C, 34.82; H, 4.52; N, 18.46; S, 16.90. Found: C, 34.93; H, 4.50; N, 18.17; S, 16.66.

EXAMPLE 5

1-(β-D-Ribofuranosyl)[1,2,4]triazole-3-carbonitrile (10)

7 A solution of 1-(2′,3′,5′-tri-O-acetyl-β-D-ribofuranosyl) [1,2,4]triazole-3-carbonitrile (20 g, 56.8 mmol) in ice-cold methanolic HCl (0.5 N, 250 mL) was kept at 0° for 24 h. Solvent was removed in vacuo and the resulting oil (12.0 g, 91%) which was homogeneous on tlc was used directly for the next step without purification; $^1$H NMR (DMSO-d$_6$)δ3.60 (m, 2H, C$_5$H); 3.96 (m, 1H, C$_4$H); 4.11, 4.32 (2m, 2H, C$_2$H and C$_3$H); 4.96, 5.26, 5.68 (t, 2d, 3H, —OH); 5.89 (d, 1H, J =3.54 Hz, C$_1$H); 9.15 (s, 1H, triazole ring proton).

EXAMPLE 6

1-(2′,3′-Di-O-isopropylidene-β-D-ribofuranosyl)[1,2,4]-triazole-3-carbonitrile (11)

A suspension of 1-(β-D-ribofuranosyl)[1,2,4]triazole-3-carbonitrile (10) (12.0 g, 52.1 mmol) in a mixture of acetone (200 mL) and dimethoxypropane (100 mL) was treated in a manner identical to the synthesis of compound 5 to yield 11 (10.78 g, 76.3%) as a colorless oil; $^1$H NMR (DMSO-d$_6$)δ6 1.32, 1.49 (2s, 6H, isopropylidene methyls); 3.44 (m, 2H, C$_5$H); 4.32 (m, 1H, C$_4$H); 4.96 (t, 1H, —OH); 4.88, 5.19 (2m, 2H, C$_2$H and C$_3$H); 6.25 (s, 1H, C1H); 9.07 (s, 1H, triazole ring proton). Anal. (C$_{11}$H$_{14}$N$_4$O$_4$) Calcd.: C, 49.62; H, 5.30; N, 21.04. Found: C, 49.50; N, 5.35; N, 20.91.

EXAMPLE 7

1-(5′-O-Sulfamoyl-2′,3′-di-O-isopropylidene-β-D-ribofuranosyl) [1,2,4]triazole-3-carbonitrile (12)

To a solution of 1-(2′,3′-di-O-isopropylidene-β-D-ribofuranosyl)[1,2,4]triazole-3-carbonitrile (11) (13.81 g, 51.8 mmol) in dry tetrahydrofuran (200 mL) cooled to 0° in an ice salt bath was added sodium hydride (8.3 g, 60% dispersion in oil). The suspension was stirred at 0° for 10 min. and a solution of sulfamoyl chloride (11.91 g, 103.1 mmol) in dry tetrahydrofuran (50 mL) was added dropwise, maintaining the temperature of the reaction mixture at 0°. The mixture was stirred at 0° for 2 h and at room temperature for 4 h. The mixture was cooled to 0°, and ethanol (25 mL) added, followed by a saturated aqueous solution of ammonium chloride (25 mL). The mixture was concentrated in vacuo and chromatographed over silica gel (flash chromatography) using 15% acetone in chloroform to yield 12 (8.8g, 50%) as an oil; $^1$H NMR (DMSO-d$_6$) δ1.32, 1.50 (2s, 6H, isopropylidene methyls); 4.10 (m, 2H, C$_5$H); 4.50, 4,95, 5.21 (3m, 3H, C$_2$, C$_3$ and C$_4$ protons); 6.41 (s, 1H, C$_1$H); 7.58 (s, 2H, —SO$_2$NH$_2$); 9.07 (s, 1H, triazole ring proton). Anal. (C$_{11}$H$_{15}$N$_5$O$_6$S) Calcd.: C, 38.26; H, 4.38; N, 20.28; S, 9.28. Found: C, 38.31; H, 4.39; N, 20.30; S, 9.08.

EXAMPLE 8

1-(5'-O-Sulfamoyl-β-D-ribofuranosyl)[1,2,4]triazole-3-carboxamide (2)

A solution of 6 (5.43 g, 14.9 mmol) in 80% acetic acid aqueous was heated to 100° for 2 h. The mixture was concentrated to dryness in vacuo, and the residue crystallized from ethanol to yield 2 (4.48 g, 93%) as an analytically pure crystalline solid; m. p. 160°d; $^1$H NMR (DMSO-d$_6$)δ5.48, 5.76 (2d, 2H, —OH); 5.92 (d, 1H, J=3.2 Hz, C$_1$H); 7.59 (s, 2H, SO$_2$NH$_2$); 7.68, 7.88 (2s, 2H, —CONH$_2$); 8.83 (s, 1H, triazole ring proton) and other sugar protons. Anal. (C$_8$H$_{13}$N$_5$O$_7$S) Calcd.: C, 29.72; H, 4.05; N, 21.66; S, 9.92. Found: C, 29.89; H, 3.96; N, 21.44; S, 9.84

EXAMPLE 9

1-(5'-O-Sulfamoyl-β-D-ribofuranosyl)[1,2,4]triazole-3-thiocarboxamide (3)

A solution of 9 (1.7 g, 4.5 mmol) in 80% aqueous acetic acid aqueous was heated to 100 for 4 h. The mixture was concentrated to dryness in vacuo and the residue was chromatographed over silica gel (flash chromatography) using 10% methanol in dichloromethane as eluent to yield 3 (0.95 g, 62.5%) as a yellow solid; m. p. 173°–175° d; $^1$H NMR (DMSO-d$_6$)δ4.0–4.33 (3m, 5H, sugar protons); 5.46, 5.77 (2d, 2H, —OH); 5,89 (d, 1H, J=2.7 Hz, C$_1$H); 7.58 (s, 2H, —SO$_2$NH$_2$); 8.80 (s, 1H, triazole ring proton); 9.54, 10.02 (2s, 2H, —CSNH$_2$) Anal. (C$_8$H$_{13}$N$_5$O$_6$S$_2$) Calcd.: C, 28.32; H, 3.86; N, 20.64; S, 18.90. Found: C, 28.51; H, 3.91; N, 20.40; S, 18.80.

EXAMPLE 10

1-(5'-0-Sulfamoyl-β-D-ribofuranosyl)[1,2,4]triazole-3-carbonitrile (4)

A solution of 13 (7.7 g, 22.3 mmol) in 80% aqueous acetic acid was heated to 100° for 2 h. The mixture was concentrated to dryness in vacuo and the residue dissolved in methanol (50 mL). The resulting solution was concentrated to dryness in vacuo and the residue crystallized from methanol/ether to yield 14 (6.47 g, 95%) as a crystalline solid; m. p. 153°–154 ; 1H NMR (DMSO-d6)δ4.0–4.40 (3m, 5H, sugar protons); 5.53, 5.83 (2d, 2H, —OH); 6.0 (d, 1H, J=2.9 Hz, C$_1$H); 7.58 (s, 2H, —SO$_2$NH$_2$); 9.10 (s, 1H, triazole ring proton). Anal. (C$_8$H$_{11}$N$_5$O$_6$S) Calcd.: C, 31.48; H, 3.63; N, 22.94; S, 10.50. Found: C, 31.56; H, 3.37; N, 23.12; S, 10.49.

Antiparasitic Activity:

The antiparasitic activities of the 1-(5'-0-sulfamoyl-β-D-ribofuranosyl)[1,2,4]triazolo 3-carboxamide, 3-thiocarboxamide and 3-carbonitrile compounds of the invention are shown in various in vitro and in vivo systems. For demonstrating the antiparasitic properties of the compounds of the invention the following representative organisms were utilized: the pathogenic hemoflagellates *Leishmania donovani, Trypanosoma brucei* and *Trypanosoma qambiense* and the enteric protozoan pathogens *Giardia lamblia* and *Trichomonas vaqinalis*. These are representative of the protozoan diseases: leishmaniasis, trypanosomiasis, giardiasis and trichomoniasis.

Culture Techniques:

*Leishmania donovani* (ATCC #30142)) and *Trypanosoma qambiense* (TH114, obtained from R. Brun, Schweizer Tropeninstitut, Basel, Switzerland) were grown in THOSMEM, HOSMEM and PPDM-79 media respectively as described in J. J. Marr, R. L. Berens and D. J. Nelson, J. Science. 202, 1018 (1978), J. J. Marr, D. J. Nelson and R. L. Berens, *Biochim. Biophys. Acta*, 544, 360 (1978) and W. R. Fish, J. J. Marr and R. L. Berens, Biochim. *Biophys. Acta*, 714, 422 (1982). For drug sensitivity studies these organisms were grown in 10 ml of their respective media in 25 cm$^2$ tissue culture flasks. Cultures were inoculated to a cell density of ≈105/ml and incubated for 5 days at 26° C. in a 5% CO$_2$ atmosphere. Final cell density was determined by counting the cells on a Coulter Counter (Model ZBI); control cultures reached a final density of ≈2·10$^7$/ml.

*Giardia lamblia* (PI, ATCC #30888) and *Trichomonas vaqinalis* (ATCC #3301) were grown in modified TYI medium in 13×100 mm screw cap tubes as described in R. L. Berens and J. J. Marr, *Biochem. Pharm.*, 35, 4191 (1986). Cultures were inoculated at a density of 10$^4$ and incubated for 3 days at 37° C.; control cultures reached densities of ≈1-2·10$^6$ for *G.* lamblia and ≈6–7·10$^6$ for *T. vaqinalis*. These parasites were counted by chilling tubes on ice for 30 min., then reading the optical density at 650 nm in a Gilford 300-N micro-sample spectrophotometer. Their cell number was obtained by comparing the absorbance to a standard curve constructed from numbers obtained by counting cells in a hemocytometer.

Drug stock solutions were prepared by dissolving the compounds of the invention in 0.1N NaOH and adjusting the final concentration to 2 mg/ml based on extinction coefficient. Drug was added to respective culture media (<2% v/v) and the media filter sterilized. Doses effective against 50% (ED50) and 90% (ED90) were determined by triplicate counting of organisms exposed to various drug concentrations and determining a mean value. Results were expressed as a percentage control.

Animals:

Antiparasitic activity of the compounds of the invention in animals against *T. brucei* EATRO 110 was determined as described in C. J. Bacchi, R. L. Berens, H. C. Nathan, R. S. Klein, I. A. Elegbe, K. V. Rao, P. P. McCann and J. J. Marr, *Antimicrob. Agents Chemother.*, 31, 1403 (1987) utilizing the mouse model described therein.

Antiparasitic activity of the compounds of the invention in animals against *L. donovani* was determined in a manner similar to that previously described J. S. Keithly and S. G. Langreth, *Amer. J. Trop. Med. Hyg.*, 32, 485 (1983) for a hamster model. Briefly, mice were infected with 5×10$^7$ stationary phase promastigotes subcultured in Schneider's drosophila medium with 15% heat inactivated fetal bovine serum. The compounds of the invention were administered by gavage nine days after infection and continued for one week. Positive controls received Pentostam intraperitoneally.

Infected, untreated controls received water orally but no intraperitoneal sham injections. Mice were necropsied sixteen days after infection (seven days after the beginning of drug treatment).

EXAMPLE 11

In this example the in vitro antiparasitic activity of the compounds of the invention was demonstrated for Leishmania donovani, Trypanosoma qambiense, Giardia lamblia and Trichomonas vaqinalis. As shown in Table I, compound 2 was the most active and had the lowest $ED_{50}$ against these organisms. T. qambiense was sensitive to each of the compounds of the inventions however as with L. donovani it was killed by low concentrations of 2 compared to 3 and 4. Compared to compound 2, compounds 3 and 4 required slightly higher concentrations for activity, i.e. $ED_{50}$ 0.5 and 1–5 μg/ml against T. gambiense and 2.5 and 1–5 μg/ml against L. Donovani for compounds 3 and 4 respectively. The mucosal pathogen G. lamblia responded to concentrations of 2 which could be achieved by non-absorbable compound. For this mucosal pathogen, the active concentrations of 3 and 4 are about the same as for compound 2. Compound 3 exhibited greater activity than compounds 2 or 4 against T. vaqinalis.

TABLE I

In vitro antiparasitic activity against various pathogens

| Organism | Compound ($ED_{50}$) (μg/ml) | | |
|---|---|---|---|
| | 2 | 3 | 4 |
| Leishmania donovani | 0.03 | 2.5 | 1–5 |
| Trypanosoma gambiense | 0.01–0.05 | 0.5 | 1–5 |
| Giardia lamblia | 5–10 | >25 | >25 |
| Trichomonas vaginalis | >25 | 15 | >25 |

Note:
Compound 2 was toxic to U-937 cells (10% Control @ 1μg/ml)

EXAMPLE 12

In this example compound 2 was tested against T. brucei. in animals. This studied augments the significant active of compound 2 as demonstrated above against T. qambiense. As is shown in Table II, compound 2 shows intraperitoneal, intravenous and oral activity against the T. brucei pathogen. It is noteworthy that the oral activity of compound 2 is greater than intraperitoneal activity. In this test compound prolonged survival at all dosages tested. The research chemical 9-deazainosine was used as a reference for this test.

TABLE II

Antiparasitic activity against T. brucei EATRO 110 in animals

| Compound | Dose (Route) | Average Survival (Days) | Range of Survival | % Cured |
|---|---|---|---|---|
| — | — | 3.4 | 3–5 | 0 |
| 2 | 1 mg/kg (i.p.) | 4.6 | 4–5 | 0 |
| | 5 mg/kg (i.p.) | 4.8 | 4–6 | 0 |
| | 10 mg/kg (i.p.) | 7.4 | 4–11 | 0 |
| | 20 mg/kg (i.p.) | 7.4 | 4–11 | 0 |
| | 50 mg/kg (i.p.) | 6.4 | 4–10 | 0 |
| | 50 mg/kg (p.o.) | 11.6 | 10–14 | 0 |
| | 50 mg/kg (i.v.) | 6.4 | 4–12 | 0 |
| 9-Deazainosine | 25 mg/kg (i.p.) | 35 | 35 | 100 |

Note:
Mice (groups of 5) were infected with $2 \times 10^5$ trypanosomes and treatment commenced 24 h post inoculation. Drugs were given once daily by the route indicated for 3 days.

While 9-deazainosine demonstrates cures when administered intraperitoneally, it is very difficult and expensive to synthesize and it is not orally active. Oral administration of antitrypanosomal agents is considered to be the preferred route of administration since this disease is most prevalent in non-urbanized areas located in tropical climates with little or poor medical facilities.

EXAMPLE 13

In this example the antiparasitic activity of compound 2 in animals is shown against Leishmania donovani. As is seen in Table III, compounds 2 is active in animals against this parasitic disease utilizing a mouse model of visceral leishmaniasis. Compound 2 shows good suppression of the parasites in the livers of the animals. A dose of 20 mg/kg/day decreased the infection by 50% at seven days of treatment. Pentostam, the present drug of choice for treatment of this pathogen, at it optimum dose level was utilized as a control. As is evident from Table III, compound 2 at 50 mg/kg/day exhibits a response equivalent to that of optimized Pentostam.

TABLE III

Antileishmanial activity in animals

| Compound | # Animals | Dose (mg/kg/day) | LDUs in Liver | Suppression (%) |
|---|---|---|---|---|
| None | 3 | — | 1515 ± 477 | 0 |
| Pentostam | 3 | 50 | 411 ± 245 | 73 |
| Compound 2 | 3 | 10 | 1244 ± 469 | 18 |
| Compound 2 | 3 | 20 | 765 ± 133 | 50 |
| Compound 2 | 3 | 50 | 501 ± 276 | 67 |

Note:
% Suppression = 100 − 100(LDUs of experimental/LDUs of control)

Of the compounds of the invention, the antiparasitic activity of compound 2 is particularly significant. Compound 2 exhibits significant activity as an antileishmanial agent in both in vitro (Table I) and in animals (Table III). In the latter system, it is as active as pentavalent antimony, the only therapeutic modality generally available in the clinic. At comparable mg/kg doses (not equimolar) it was as active as Pentostam (Burroughs Well come, Beckenham, England).

Compound 2 also shows antitrypanosomal activity both in vivo against T., brucei and in vitro against T. gambiense. The activity in animals is particularly significant since the compound exhibits this activity when administered orally. The animal model for African trypanosomiasis of Example 13 above has proven very useful for the study of treatment for trypanosomiasis as is shown in C. J. Bacchi et al. referenced above.

Against a giardiasis infection, of the compounds of the invention, compound exhibited the greater activity while against a trichomoniasis infection compound 3 exhibited the greater activity.

The compounds of the invention can be given to a host in need thereof in appropriate formulations wherein the compounds comprise the active ingredient of the formulations. Thus a compound of the invention can be made up into injectables suitable for intravenous or other type injection into the host. Further it can be given in an appropriate oral formulation as for instance as an oral syrup preparation, an oral capsule or oral tablet. An additional route of administration might be as a suppository.

For an injectable the compound would be dissolved in a suitable solution as for instance in a sodium bicarbonate or other buffer. Such a solution would be filtered and added to appropriate ampoules or vials and sealed and sterilized.

As a syrup, the compound in buffered solution would be mixed with an appropriate syrup with mild stirring. For capsules the dry compound would be blended with appropriate fillers, binders or the like as for instance Lactose USP powder or Sterotex powder. For the preparation of tablets the compound of the invention would be mixed with suitable binders and fillers as for instance corn starch NF, Microcrystalline Cellulose, Sterotex powder and water and dried to a low water content. This would be followed by screening, milling, further screening and pressing into the appropriate tablets.

For suppositories, the compound would be dissolved into appropriate melts of Polyethylene Glycol as for instance Polyethylene Glycol 1540 and 8000 at 60° and formed into the suppositories by molding at 25°.

In addition to the above formulations, a compound of the invention could also be administered utilizing other delivery technique such as incorporating the compound of the invention with liposomes and the like.

Additionally, prodrug forms of the compounds of the invention could be utilized to facilitate dispensing, uptake, absorption, metabolic control and the like. One such prodrug would be the diacetate ester. Further prodrugs might allow for enzymatic conversion in vivo of analogs of the compound of the invention into the compound of the invention.

We claim:

1. 1-(5'-O-sulfamoyl-β-D-ribofuranosyl)[1,2,4]-triazole-3-carboxamide.

2. 1-(5'-O-sulfamoyl-β-D-ribofuranosyl([1,2,4]-triazole-3-thiocarboxamide.

3. 1-(5'-O-sulfamoyl-β-D-ribofuranosyl([1,2,4]-triazole-3-carbonitrile.

4. A pharmaceutical composition comprising:
an antiparasitic effective amount of a compound selected from the group consisting of 1-(5'-O-sulfamoyl-β-D-ribofuranosyl)[1,2,4]triazole-3-carboxamide, 1-(5'-O-sulfamoyl-β-D-robpfiramp-su;)[1,2,4]triazole-3-carbonitrile; and a pharmaceutical carrier thereof.

5. A pharmaceutical composition of claim 4 wherein: said compound is 1-(5'-O-sulfamoyl-β-D-ribofuranosyl)-[1,2,4]triazole-3-carboxamide.

6. A pharmaceutical composition of claim 4 wherein: said compound is 1-(5'-O-sulfamoyl-β-D-ribofuranosyl)-[1,2,4]triazole-3-thiocarboxamide.

7. A pharmaceutical composition of claim 4 wherein: said compound is 1-(5'-O-sulfamoyl-β-D-ribofuranosyl)-[1,2,4]triazole-3-carbonitrile.

* * * * *